United States Patent [19]
Carim

[11] Patent Number: 6,135,953
[45] Date of Patent: Oct. 24, 2000

[54] MULTI-FUNCTIONAL BIOMEDICAL ELECTRODES

[75] Inventor: Hatim M. Carim, West St. Paul, Minn.

[73] Assignee: 3M Innovative Properties Company, St. Paul, Minn.

[21] Appl. No.: 08/591,868

[22] Filed: Jan. 25, 1996

[51] Int. Cl.$^7$ .................................................. A61B 5/04
[52] U.S. Cl. ..................... 600/372; 600/391; 600/395; 600/396; 600/397; 607/152; 606/32
[58] Field of Search .................. 128/639, 644; 607/75, 152, 153; 600/372, 386, 391–393, 395–397; 606/32

[56] References Cited

U.S. PATENT DOCUMENTS

| | | | |
|---|---|---|---|
| 2,536,271 | 1/1951 | Fransen | 128/413 |
| 3,720,209 | 3/1973 | Bolduc | 128/2.06 E |
| 3,960,141 | 6/1976 | Bolduc | 606/32 |
| 3,976,055 | 8/1976 | Monter et al. | 128/2.06 E |
| 3,977,392 | 8/1976 | Manley | 128/2.1 E |
| 3,989,050 | 11/1976 | Buchalter | 607/75 |
| 4,352,359 | 10/1982 | Larimore et al. | 128/640 |
| 4,381,789 | 5/1983 | Naser et al. | 128/798 |
| 4,409,981 | 10/1983 | Lundberg | 128/640 |
| 4,419,998 | 12/1983 | Heath | 128/639 |
| 4,494,552 | 1/1985 | Heath | 128/696 |
| 4,522,211 | 6/1985 | Bare et al. | 128/640 |
| 4,524,087 | 6/1985 | Engel | 427/2 |
| 4,539,996 | 9/1985 | Engel | 128/640 |
| 4,554,924 | 11/1985 | Engel | 128/640 |
| 4,664,119 | 5/1987 | Bessman et al. | 128/635 |
| 4,715,382 | 12/1987 | Strand | 128/640 |
| 4,807,621 | 2/1989 | Hagen et al. | 128/303.13 |
| 4,834,103 | 5/1989 | Heath | 128/798 |
| 4,838,273 | 6/1989 | Cartmell | 128/640 |
| 4,846,185 | 7/1989 | Carim | 128/641 |
| 4,848,345 | 7/1989 | Zenkich | 128/419 |
| 4,848,348 | 7/1989 | Craighead | 128/639 |
| 4,848,353 | 7/1989 | Engel | 128/640 |
| 4,850,356 | 7/1989 | Heath | 128/419 |
| 4,852,571 | 8/1989 | Gadsby et al. | 128/640 |
| 4,852,585 | 8/1989 | Heath | 128/798 |
| 4,873,974 | 10/1989 | Hagen et al. | 128/303.13 |
| 4,895,169 | 1/1990 | Heath | 128/798 |
| 4,955,381 | 9/1990 | Way et al. | 600/393 |
| 5,012,810 | 5/1991 | Strand et al. | 128/640 |
| 5,133,356 | 7/1992 | Bryan et al. | 128/640 |
| 5,215,087 | 6/1993 | Anderson et al. | 128/640 |
| 5,225,473 | 7/1993 | Duan | 524/388 |
| 5,276,079 | 1/1994 | Duan et al. | 524/386 |
| 5,295,482 | 3/1994 | Clare et al. | 128/639 |
| 5,299,572 | 4/1994 | Chen et al. | 128/639 |
| 5,337,748 | 8/1994 | McAdams et al. | 128/640 |
| 5,338,490 | 8/1994 | Dietz et al. | 252/500 |
| 5,352,315 | 10/1994 | Carrier et al. | 156/267 |
| 5,354,321 | 10/1994 | Berger | 607/75 |
| 5,360,440 | 11/1994 | Andersen | 607/75 |
| 5,362,420 | 11/1994 | Itoh et al. | 252/500 |
| 5,385,679 | 1/1995 | Uy et al. | 252/500 |
| 5,496,363 | 3/1996 | Burgio et al. | 607/152 |

FOREIGN PATENT DOCUMENTS

| | | | |
|---|---|---|---|
| 195 03 341 A1 | 7/1995 | Germany | A61H 39/00 |
| 653897A | 1/1986 | Switzerland | 607/75 |
| WO 93/02616 | 2/1993 | WIPO | A61B 5/04 |
| WO 94/12585 | 6/1994 | WIPO | C09J 171/00 |
| WO 94/26950 | 11/1994 | WIPO | C23C 14/20 |
| WO 94/27491 | 12/1994 | WIPO | A61B 5/00 |
| WO 95/20350 | 8/1995 | WIPO | A61B 5/0408 |
| WO 95/20634 | 8/1995 | WIPO | C09J 7/02 |

*Primary Examiner*—Linda C. M. Dvorak
*Assistant Examiner*—David M. Ruddy
*Attorney, Agent, or Firm*—Robert W. Sprague

[57] ABSTRACT

A multi-functional, differing electrochemical potential biomedical electrode is disclosed. Several embodiments are described based on the difference in composition of multiple conductors, the difference in composition of fields of ionically conductive media, or both on a single insulative backing of a tab/pad style electrode. A galvanic circuit can be created from electrodes of the present invention, permitting self-restoration of defibrillation recovery of monitoring electrodes and the powering of iontophoretic delivery of pharmaceuticals, among other uses.

23 Claims, 1 Drawing Sheet

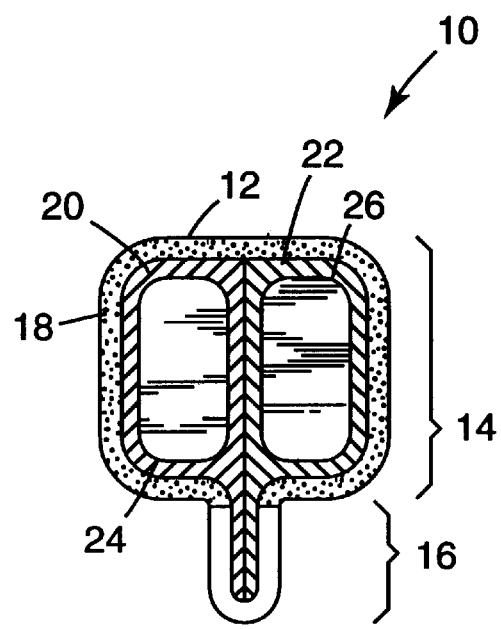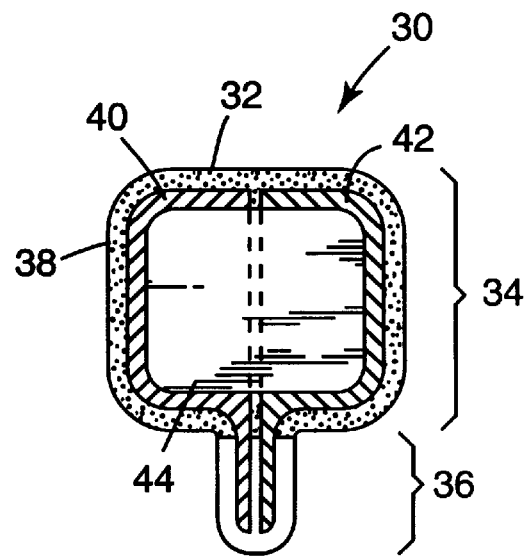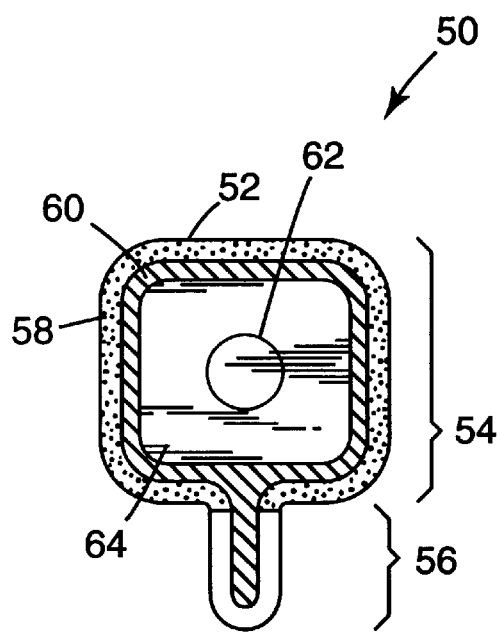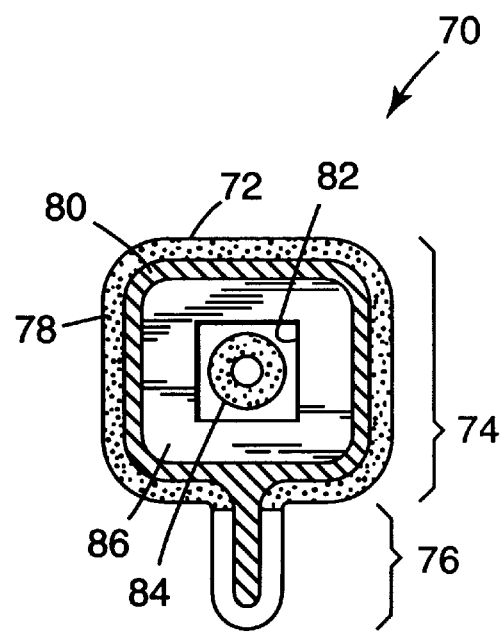

MULTI-FUNCTIONAL BIOMEDICAL ELECTRODES

FIELD OF THE INVENTION

This invention concerns biomedical electrodes having multiple functions.

BACKGROUND OF THE INVENTION

Modern medicine uses many diagnostic procedures where electrical signals or currents are received from a mammalian patient's body. Nonlimiting examples of diagnostic procedures include electrocardiographic (ECG or EKG) diagnosis or monitoring of electrical wave patterns of a mammalian heart, irrespective of duration or circumstance. The point of contact between medical equipment used in these procedures and the skin of the patient is usually some sort of biomedical electrode. Such an electrode typically includes a conductor which must be connected electrically to the equipment, and an ionically conductive medium adhered to or otherwise contacting skin of a patient.

Among diagnostic procedures using biomedical electrodes are monitors of electrical output from body functions, such as electrocardiographs (ECG) for monitoring heart activity and for diagnosing heart abnormalities.

For each diagnostic procedure, at least one biomedical electrode having an ionically-conductive medium containing an electrolyte is adhered to or otherwise contacting skin at a location of interest and also electrically connected to electrical diagnostic equipment. A critical component of the biomedical electrode is the electrical conductor in electrical communication with the ionically-conductive medium and the electrical diagnostic equipment.

Electrical conductors require excellent electrical conductivity and minimal electrical resistance for biomedical electrodes, especially when faint electrical signals are received from the patient. For this reason, metals or carbon (especially graphite) are used. Among metals, silver is preferred because of its optimal conductivity. But biomedical electrodes which monitor a patient's conditions must have a stable half cell potential and be able to withstand the polarizing effects of a defibrillation procedure for a heart. For this reason, a metal halide, such as silver chloride, is preferably used with a metal conductor, such as silver, to create a depolarizable electrical conductor in biomedical electrodes which can monitor a heart.

One principal difficulty with a biomedical electrode containing silver/silver chloride is the expense of silver.

Others have attempted to reduce the cost of silver in biomedical electrodes by using graphite or other galvanically inactive materials in association with silver particles or silver/silver chloride layers. See, for example, U.S. Pat. Nos. 3,976,055 (Monter et al.) and 4,852,571 (Gadsby et al.).

Others have used other galvanically inactive electrical conductors in biomedical electrodes. See, for example, U.S. Pat. Nos. 4,846,185 (Carim), which discloses ferrous/ferric chloride and galvanically inactive metals and PCT Patent Publication No. WO 95/20350 (Takaki), which discloses galvanically inactive inorganic oxides in a galvanically inactive binder.

Others have combined the purposes of biomedical electrodes to accomplish both diagnosis/monitoring of bioelectric signals with delivery of therapeutic electrical signals into the body of a patient. See, for example, U.S. Pat. Nos. 4,419,998; 4,494,552; 4,834,103; 4,848,103; 4,848,345; 4,850,356; 4,852,585; and 4,895,169 (all Heath); and PCT Publication WO 94/26950 (Robbins et al) for the use of a single electrode to both monitor bioelectric signals from the body and delivery pacing or defibrillation electrical signals to the body of a patient in need.

Others have provided multiple electrical conductors on a single biomedical electrode for a variety of purposes. See, for example, U.S. Pat. Nos. 2,536,271 (Fransen); 3,720,209 (Bolduc); 4,381,789 (Naser et al.); 4,807,621 and 4,873,974 (both Hagen et al.) for the delivery or return of high frequency energy; 5,295,482 (Clare et al.) for the creation of differing resistances on a dispersive electrode plate for electrosurgery; and PCT Publication No. WO 94/27491 (Burgio et al.) for the placement of two transcutaneous electrical nerve stimulation (TENS) electrodes on a common carrier for compact delivery of therapeutic electrical signals for intraoral procedures.

In each instance, the biomedical electrode has employed a field of conductive hydrogel or adhesive to contact or adhere to mammalian skin and to receive the electrical signals and transmit them ionically to an electrical conductor for electrical connection to biomedical instrumentation.

Representative examples of biomedical electrodes include U.S. Pat. Nos. 4,352,359 (Larimore); 4,524,087 (Engel); 4,539,996 (Engel); 4,554,924 (Engel); 4,848,348 (Carim); 4,848,353 (Engel); 5,012,810 (Strand et al.); 5,133,356 (Bryan et al.); 5,215,087 (Anderson et al.); and 5,296,079 (Duan et al.).

Biomedical electrode construction has increasingly employed a tab/pad style of construction. A number of biomedical electrode constructions have employed an insulative outer layer through which an electrically conductive tab extends to provide a low profile, multi-layer construction. Representative examples of such constructions are disclosed in the embodiments shown in U.S. Pat. No. 5,012,810 (Strand et al.).

Another low profile multi-layer construction employs an electrically conductive tab which remains below the surface of the outermost layer but is accessible to the outside through an aperture in the outermost layer. A representative example of this electrode construction is disclosed in U.S. Pat. No. 5,215,087 (Anderson et al.).

Other biomedical electrode constructions involve an elaborate placement of sponges in apertures to which an electrically conductive tab can contact even though that tab does not extend beneath the surface of the outer most layer. Representative examples of this construction is found in U.S. Pat. No. 3,977,392 (Manley), U.S. Pat. No. 4,522,211 (Bare et al.) and U.S. Pat. No. 4,838,273 (Cartmell).

Another biomedical electrode construction employs a reservoir of conductive gel into which a lead wire can be inserted through an aperture, as disclosed in U.S. Pat. No. 4,409,981 (Lundberg). Another biomedical electrode construction employs an aperture in communication with a conductive adhesive into which a lead wire can be inserted through the aperture, as disclosed in U.S. Pat. No. 4,715,382 (Strand).

Because biomedical electrodes are disposable and are generally disposed after a single use, cost/benefit analysis of biomedical electrode usage is continuously under health care cost scrutiny. The more that a single biomedical electrode can provide for the least amount of cost is a goal of both manufacturers and the consumers they serve.

For example, about 10 diagnostic biomedical electrodes are required for each electrocardiogram (ECG) procedure. Such diagnostic biomedical electrodes are presently designed for a single purpose and for a single use, making the cost of such electrodes to customers very sensitive to manufacturing techniques and performance features. Unfortunately in some diagnostic electrodes, the cost of manufacture outweighs the performance properties of the electrode.

The same cost/benefit analysis issues arise with more expensive biomedical electrodes that are used less frequently but are designed for one or more than one performance purpose.

SUMMARY OF THE INVENTION

The present invention solves problems confronting manufacturers and users of biomedical electrodes by combining multiple electrode functions on a single, inexpensive electrode due to a differing electrochemical potential on the electrode.

One aspect of the invention is a multi-functional, differing electrochemical potential biomedical electrode.

"Multi-functional" means that a single biomedical electrode of the present invention can operate or provide more than one function in conjunction with its use with the body of a patient. Nonlimiting examples of multi-functional uses of a biomedical electrode of the present invention include the ability to both deliver and receive electrical signals to and from the body of a patient; the ability to provide both a polarizable portion and a non-polarizable portion of a biomedical in communication with the body of a patient; and the ability to provide a galvanic circuit and some monitoring or therapeutic activity with the body of a patient.

A patient can be any animal for which biomedical electrodes can be used.

"Differing electrochemical potential" means that one combination of electrically conductive material and ionically conductive medium on one portion of the electrode differs in electrochemical potential from a second combination of electrically conductive material and ionically conductive medium on another portion of the same electrode. The difference in electrochemical potential can be provided by differences in the respective electrically conductive materials, by differences in the respective ionically conductive media, or by differences in both the respective electrically conductive materials and the ionically conductive media.

Several embodiments of this biomedical electrode are contemplated based on the twin goals of using two portions of an electrode having a differing electrochemical potential to provide the means of electrical communication in the biomedical electrode and of performing more than one type of electrical communication by one electrode.

One embodiment of a multi-functional, differing electrochemical potential biomedical electrode comprises a biomedical electrode having two portions to provide a differing electrochemical potential, wherein the electrode comprises at least two electrical conductors of differing compositions.

Another embodiment of a multi-functional, differing electrochemical potential biomedical electrode comprises a biomedical electrode having two portions to provide a differing electrochemical potential, wherein the electrode comprises at least two ionically conductive media of differing compositions.

One feature of the biomedical electrode is the ability to manufacture the biomedical electrode with known electrically conductive materials and known ionically conductive media and with known manufacturing techniques but in new combinations previously unknown and unexpectedly beneficial in use.

Another feature of the biomedical electrode is the ability to perform more than one means of electrical communication concurrently, intermittently, or episodically to and from the biomedical electrode in contact with the body of a patient. For example, a single biomedical electrode contemplated in the present invention can provide both electrocardiographic monitoring and pacing therapy at the same time or as needed.

Another feature of the biomedical electrode is the ability of conductors of different materials, ionically conductive media of different materials, or both, on a single electrode to create a galvanic circuit when in contact with skin of a patient. This galvanic circuit can be used for a variety of purposes due to the stored energy inherently present in the two different conductor materials, the two different ionically conductive media, or both.

An advantage of the biomedical electrode of the present invention is the reduction of the numbers of types of biomedical electrodes that must be constructed to suit various consumer needs. This advantage benefits both the manufacturer and the consumer for inventory control, improving the cost/benefit analysis confronting the health care industry.

Additional aspects, features, and advantages of the invention will become apparent in relation to embodiments of the invention as described using the following drawings.

BRIEF DESCRIPTION OF THE DRAWINGS

FIG. 1 is a bottom plan view of one embodiment of a biomedical electrode of the present invention.

FIG. 2 is a bottom plan view of a second embodiment of a biomedical electrode of the present invention.

FIG. 3 is a bottom plan view of a third embodiment of a biomedical electrode of the present invention.

FIG. 4 is a bottom plan view of a fourth embodiment of a biomedical electrode of the present invention.

For purposes of illustration only in the bottom plan views, the fields of ionically conductive media are shown within the perimeter of the electrical conductors. However, as known to those skilled in the art, the fields of conductive media normally extend to and preferably extend beyond the perimeter of the electrical conductors.

EMBODIMENTS OF THE INVENTION

Referring to FIG. 1, one embodiment of a biomedical electrode 10 is shown from the bottom side that contacts the body of a patient.

Electrode 10 comprises an electrically insulative backing 12 in the form of a pad portion 14 and a tab portion 16. Backing 12 optionally has a field 18 of biocompatible pressure sensitive adhesive on its bottom surface. Multiple, contiguous electrical conductors 20 and 22 contact the backing 12 (preferably adhering to field 18) on the pad portion 14 and extend to the tab portion 16. Two discontiguous ionically conductive media fields 24 and 26 of conductive hydrogel or adhesive contact and preferably completely covers or extends beyond the perimeter of contiguous conductors 20 and 22, respectively in pad portion 14. The fields 18, 24, and 26 are protected by a conventional release liner (not shown).

Conductors 20 and 22 can be made from different compositions of electrically conductive materials when the differing electrochemical potential is principally derived from the conductor portions of the electrode 10. One conductor is constructed from materials that are more galvanically active than the other conductor. Desirably, one conductor is constructed from materials that are more electron donating than the other conductor. Preferably, one conductor is constructed from galvanically active materials with the other conductor being constructed from galvanically inactive materials.

The choice of materials for conductors 20 and 22 can vary according to the needs of those skilled in the art of making and using biomedical electrodes. For example, an acceptable biomedical electrode could be made using differing conductors where one conductor was more galvanically active than the other conductor in order to establish a weak galvanic circuit formed from the contiguity of the two conductors 20 and 22 and the body of a patient contacting different fields 24 and 26 of conductive adhesive. As described later, creation of a galvanic circuit can have several benefits for multifunctional biomedical electrodes.

Nonlimiting examples of electrically conductive materials used in the construction of conductors 20 and 22 include galvanically active metals (e.g., zinc, magnesium, tin, aluminum, and silver); galvanically inactive metals (e.g., platinum, gold, and selected alloys such as stainless steels); galvanically inactive inorganic oxides (e.g., manganese dioxide); carbon (e.g., graphite) and combinations thereof.

Desirably, the two conductors 20 and 22 are constructed with one electrically conductive material capable of donating electrons with the other electrically conductive material capable of accepting electrons. For example, when used with an appropriate composition of conductive adhesive fields 24 and 26, if conductor 20 is made of graphite and conductor 22 is made of silver, then with the creation of a circuit, graphite in conductor 20 accepts electrons given by silver in conductor 22. This miniature battery formed from a galvanic circuit can both treat a patient, restore a monitoring function after defibrillation of the heart of a patient, and can power other therapy functions resident to or connected by circuitry to electrode 10. The electrode 10 can also be reconditioned by the biomedical instrumentation. Other examples for conductor 22 as an electron donor are zinc, aluminum, tin, and magnesium, while examples for conductor 20 as an electron acceptor are silver/silver chloride and tin/stannic chloride.

Preferably, the two conductors 20 and 22 are constructed with one electrically conductive material being galvanically active and the other material being galvanically inactive. The graphite conductor 20/silver conductor 22 example in the preceding paragraph also is applicable in this preferred construction to maximize the stored energy available in electrode 10.

In addition to the use of different electrically conductive materials on conductors 20 and 22, one can use two different layers of galvanically active and galvanically inactive materials on any one conductor surface for either conductor 20, 22, or both. Unlike the teaching of Gadsby et al. (which required a layer of galvanically active metal at least partially covering a layer of galvanically inactive carbon-containing material), and unlike the teaching of Monter et al., (which required a minimally useful amount of galvanically active metal at the surface of a galvanically inactive composite material), the present invention unexpectedly finds advantages to the use of a layer of galvanically active metal contacting backing with a layer of galvanically inactive material covering the metal and contacting ionically conductive media. While this combination of layers does not, itself, provide a "nonpolarizable" electrode, one can be made from this construction with other materials with their attendant advantages. Thus, this embodiment of the invention is directly opposite the conventional teachings of the use of galvanically active and galvanically inactive materials.

This embodiment of the present invention additionally contemplates any combination of galvanically active materials with galvanically inactive materials where the latter form the layer which contacts the conductive hydrogel or adhesive. Desirably, the galvanically active metal is aluminum or silver and the galvanically inactive material is graphite, which in this context contemplates graphite also serving as a catalytic surface for the underlying metal. Preferably, the galvanically active metal is silver. Alternatively, the galvanically active metal can be of lower quality and cost, if graphite is the outer layer. An expensive conductor can be constructed without a functional decrease in acceptable performance.

The galvanically active metal layer can range from about 100 nm to about 500 $\mu$m and preferably ranges from about 300 nm to about 300 $\mu$m. with the galvanically inactive material in a dried thickness ranging from about 1 $\mu$m to about 1 mm, and preferably in a thickness of about 200 $\mu$m.

Having the galvanically inactive material covering the galvanically active metal and also contacting the ionically conductive media unexpectedly provides the following advantages: the use of the more expensive galvanically active metal is minimized; a highly electrically conductive substrate is created; the lower cost galvanically inactive graphite conductor is maximized. Additionally, when the teachings of U.S. Pat. No. 4,846,185 (Carim) are used, redox couple containing electrolyte compositions should use a galvanically inactive surface provided by this embodiment.

At least a portion of conductors 20 and 22 at tab portion 16 can be contacted by a clamp or connector for electrical communication with biomedical electrical instrumentation, either to transmit energy into a body such as that used in transcutaneous electrical nerve stimulation or for receiving electrical signals from the body such as that used in electrocardiography. Alternatively, tab portion 16 can have a stud/eyelet combination known to those skilled in the art to provide a snap connection at each conductor 20 and 22.

Selection of materials for use in insulative backing 12 follows the choices of one skilled in the art and can employ any of the materials described in the patents and publications identified in the Background of the Invention above.

When an optional field 18 of pressure sensitive adhesive is employed, then the perimeter of backing 12 has field 18 of pressure sensitive adhesive extending beyond the perimeter of conductors 20 and 22 such that field 18 becomes a skirt of pressure sensitive adhesive to adhere electrode 10 to skin of a patient.

Nonlimiting examples of a suitable backing for use in the present invention are medical-grade pressure sensitive adhesive tapes such as those commercially available under the brands "Blenderm" or "Durapore" or a melt blown polyurethane material having a pressure sensitive adhesive coating on its major surface, such as that disclosed in U.S. Pat. No. 5,230,701 (Riedel).

Backing 12 has a thickness ranging from about 0.02 mm to about 0.89 mm and preferably 0.35 mm in order to provide a low profile layer of the multi-layer construction.

Selection of materials for use in fields 24 and 26 of conductive hydrogel or adhesive follows the choices of one skilled in the art and can employ any of the materials described in the patents and publications identified in the Background of the Invention above.

Fields 24 and 26 can be made from the same or different ionically conductive media depending on which embodiment of the differing electrochemical potential electrode is desired. If the same, then different performances of electrode 10 resides in the choices of conductors 20 and 22 to provide a differing electrochemical potential electrode. If different, then different performances of the conductors on the electrode 10 are also affected by the different ionically conductive media fields 24 and 26, whether conductors 20 and 22 are made from the same material.

Nonlimiting examples of ionically conductive media useful as either field 24 or field 26, or both, in electrode 10 of the present invention include those ionically conductive compositions disclosed in U.S. Pat. Nos. 4,524,087 (Engel), 4,539,996 (Engel), 4,848,353 (Engel); 4,846,185 (Carim); 5,225,473 (Duan); 5,276,079 (Duan et al.); 5,338,490 (Dietz et al.); 5,362,420 (Itoh et al.); 5,385,679 (Uy et al.); copending, coassigned applications PCT Publication Nos. WO 95/20634 and WO 94/12585 and copending coassigned PCT Patent Application Ser. Nos. US95/17079 (Docket No. 51537PCT4A); US95/16993 (Docket No. 5129UPCT8A); and US95/16996 (Docket No. 48381PCT1A), the disclosures of which are incorporated by reference herein. In order to provide the differing electrochemical potential, field 24 and field 26 can be selected from different ionically conductive media from any combination of the compositions disclosed above. One specific reference, U.S. Pat. No. 4,846,185 (Carim), discloses the use of a redox couple containing electrolyte composition where one field 24 can have one composition of the couple and the other field 26 can have the composition of the redox couple.

Another example of differing ionically conductive media for fields 24 and 26 is the use of an oxidizable composition for field 24 and a reducible composition for field 26. For example, a reducible composition for field 26 comprises an aqueous conductive adhesive with dissolved oxygen therein.

Yet another example of differing ionically conductive media for fields 24 and 26 is the use of a composition for field 24 that provides ions, such as hydronium ions, to the corresponding electrical conductor and the use of a composition for field 26 thaioprovides species that will form chemical bonds with ions from the corresponding electrical conductor. Nonlimiting examples of this embodiment are the use of hydroxyl ions to form metal hydroxides in the ionic field and the use of carboxylate groups such as in the compositions disclosed in U.S. Pat. No. 4,524,087 (Engel) that complex with ions of or from the electrical conductor. Other complexing agents are known as chelating agents such as EDTA, citrate salts, and the like.

Thickness of the ionically conductive media fields 24 and 26 can range from about 0.25 mm to about 2.5 mm and preferably 0.63 mm in order to maintain a low profile, multi-layer biomedical electrode construction.

Conventional release liners known to those skilled in the art of making biomedical electrodes can be used on electrode to cover fields 18, 24, and 26 during storage until usage. A typical release liner is a siliconized paper commercially available as Polyslik™ liner from Rexam Release of Oakbrook, Ill.

FIG. 2 illustrates a second embodiment of the present invention. Electrode 30 comprises an electrically insulative backing 32 having a pad portion 34 and a tab portion 36. A field 38 of biocompatible pressure sensitive adhesive optionally covers backing 32 and provides adhesiveness of electrode 30 for contact with the body of a patient.

Electrode 30 differs from electrode 10, in that conductors 40 and 42 are discontiguous and separated so that there is no electrically contact between their adjacent perimeters. Electrode 30 also differs from electrode 10, in that there is a single field 44 of ionically conductive medium contacting and preferably completely covering or extending beyond the perimeter of both conductors 40 and 42 in pad portion 34.

Electrode 30 provides a different geometry for the creation of a galvanic circuit, because electrode 30 does not rely on the body of a patient to provide the completion of the galvanic circuit. Rather, electrical connection to a clamp, other electrical devices, or the biomedical instrumentation completes the circuit.

Materials for electrode 30 can be any of the materials described above for electrode 10 and can be chosen in the same way for the same reasons by one skilled in the art. Preferably, conductors 40 and 42 contain silver and graphite, respectively.

FIG. 3 illustrates a third embodiment of the present invention. Electrode 50 comprises an electrically insulative backing 52 having a pad portion 54 and a tab portion 56. A field 58 of biocompatible pressure sensitive adhesive optionally covers backing 52 and provides adhesiveness of electrode 50 for contact with the body of a patient.

Electrode 50 differs from electrode 10, in that conductor 60 surrounds conductor 62. Electrode also differs from electrode 10, in that there is a single field 64 of ionically conductive medium contacting and preferably completely covering or extending beyond the perimeter of both conductors 60 and 62 in pad portion 54.

Electrode 50 provides a different geometry for the use of combination electrode where the use of conductor 60 is primarily at the perimeter of conductor 60 in a manner as described and utilized in U.S. Pat. No. 5,337,748 (McAdams et al.) and the Clare patent described above. In other words, the non-perimeter portions of conductor 60 do not substantially contribute to the function of electrode 50 for the purposes of defibrillation because the majority of the current will flow at the edges of a sheet conductor, not at its central area. Away from the perimeter of conductor 60 resides conductor 62, which can rely on conductor 60 for electrical connection or can use a separate electrical connection (not shown).

One use of electrode 50 can be concurrent uses such as having conductor 60 be a dispersive plate for electrosurgery and having conductor 62 be a monitoring electrode during electrosurgery. Because conductors 60 and 62 are contiguous and field 64 of ionically conductive media contacts both conductors 60 and 62, a galvanic circuit is created within electrode 50.

However, materials for electrode 50 can be any of the materials described above for electrode 10. Preferably, conductors 60 and 62 contain aluminum and graphite, respectively. Additionally graphite conductor 62 could also contain a third metal or metal/metal salt such as Ag/AgCl.

FIG. 4 illustrates a fourth embodiment of the present invention. Electrode 70 comprises an electrically insulative backing 72 having a pad portion 74 and a tab portion 76. A field 78 of biocompatible pressure sensitive adhesive optionally covers backing 72 and provides adhesiveness of electrode 70 for contact with the body of a patient.

Electrode 70 differs from electrode 50, in that conductor 80 surrounds an aperture 82 in which a second conventional biomedical electrode 84 can reside. Electrode 70 also differs from electrode 50, in that there is a single field 86 of ionically conductive medium contacting and preferably completely covering or extending beyond the perimeter of conductor 80 in pad portion 74 but not aperture 82.

Biomedical electrode 84 can be a conventional biomedical electrode known to those skilled in the art or can be an electrode of this invention such as electrode 10 or 30. Because electrode 84 resides in aperture 82 of electrode 70, for purposes of this invention as alternative embodiment to electrode 50, this combination of electrode 70 and electrode 84 is considered a multi-functional, multiple conductor electrode within the scope of the present invention.

One use of electrode 70 can be concurrent uses such as having conductor 80 be a dispersive plate for electrosurgery and having electrode 84 be a monitoring electrode during electrosurgery. Because conductor 80 and electrode 84 are discontiguous and field 86 of ionically conductive media contacts only conductor 80, a galvanic circuit is not possible. However, a galvanic circuit can be formed if desired by connecting the leads to the conductor 80 and electrode 84 externally, such as at the biomedical instrumentation.

However, materials for electrode 50 can be any of the materials described above for electrode 10.

Method of Making the Invention

Electrodes 10, 30, 50, and 70 can be made using conventional tab/pad style electrodes as described in those patents identified in the Background of the Invention. Generally, multiple layered electrodes are assembled from rolls of starting materials for insulative backing, upon which is coated or painted conductors, upon which is coated or cured ionically conductive media. Generally, an array of electrodes are constructed in line and cut into individual electrodes on a single release liner.

Materials for conductors 20, 22, 40, 42, 60, 62, and 80 can be formed from inks, paints, or laminates. Preferably conductors are formed from electrically conductive inks printed in registration on a backing. Commercially available inks for biomedical electrodes include Ercon branded inks, Acheson Colloid branded inks, as well as those ink sources identified in the patents identified in the Background of the Invention above.

Automated machinery can be employed to make electrodes 10, 30, 50, or 70. One skilled in the art of making electrodes can select from a variety of machinery manufacturers and manufacturing techniques to minimize manufacturing expense and waste. Some types of machinery are disclosed in U.S. Pat. Nos. 4,715,382 (Strand); 5,133,356 (Bryan et al.); and copending, coassigned U.S. patent application Ser. No. 08/343,353 (Kantner et al.), the disclosures of which are incorporated by reference herein. Another method of manufacturing biomedical electrodes is disclosed in U.S. Pat. No. 5,352,315 (Carrier et al.)

Usefulness of the Invention

Multi-function, multiple conductor biomedical electrodes of the present invention can be used for a variety of purposes according to the needs of consumers in the health care industry.

Nonlimiting examples of uses of electrodes 10, 30, 50, and 70 include combination biomedical electrodes for diagnosis/monitoring of bioelectric signals from a body and therapeutic delivery of electrical signals into a body; providing a combination of an electrode signature or other electrode performance information for adaptive/intelligent biomedical instrumentation while also diagnosing or monitoring the patient; providing a combination of monitoring a patient at the area where a dispersive plate electrode is being used for electrosurgery; monitoring a patient at the area where an external cardiac pacing electrode is being used or where an external defibrillation electrode is being used.

Nonlimiting examples of delivering of electrical signals to a patient include TENS, transdermal drug delivery, electroporation, iontophoresis, external cardiac pacing, electrophysiological assessement, and reducing impedance or otherwise conditioning skin of a patient. These and other therapeutic uses of biomedical electrodes are disclosed in copending, coassigned U.S. patent application Ser. No. 08/591,867, (Attorney Docket 52022USA4B), the disclosure of which is incorporated by reference herein.

For example, a combination electrode can both provide monitoring functions and iontophoresis. If electrodes 10 or 30 are used, a galvanic circuit can be employed to power the delivery of a pharmaceutical or other therapeutic agent in the iontophoretic function of electrode 10 or 30. Otherwise, biomedical instrumentation can be used to power electrode 10 or 30.

For example, a combination electrode 10 or 30 with one conductor containing silver/silver chloride and another conductor containing graphite can employ the galvanic circuit described above to restore the silver chloride after a defibrillation of a patient using electrode 10 or 30 functioning as a pacing or defibrillation electrode in combination with a monitoring electrode that requires defibrillation recovery properties to meet Association for the Advancement of Medical Instrumentation (AAMI) standards.

For example, a combination electrode 10 or 30 with one conductor containing a galvanically active material and the other conductor containing a galvanically inactive material with an appropriate electrolyte can function as a self-powered monitoring electrode and battery for powering other circuitry for remote telemetric communication of the condition of a patient, where electricity and/or telephone communications are lacking or not needed. Battlefield triage could benefit from a self-powered monitoring electrode.

Nonlimiting examples of uses of providing unique electrode identification information (an "electrode signature") or other electrode performance information for adaptive/intelligent biomedical instrumentation include identification of the proper electrode for usage, continued performance of the electrode during usage, alarm conditions when the performance of the electrode has expired or is substandard, and other interaction conditions with cables and leadwires between the electrode and biomedical instrumentation. These and other adaptive/intelligent instrumentation uses are also described in copending, coassigned U.S. patent application Ser. No. 08/591,867, (Attorney Docket No. 52022USA4B) the disclosure of which is incorporated by reference herein.

Once those skilled in the art recognize the usefulness of a multifunction, multiple conductor biomedical electrode of the present invention, other uses will become apparent without departing from the spirit and scope of the present invention. With and without creation of a galvanic circuit, with and without the use of a variety of electrical conductors in contiguous or discontiguous relation to each other, and with and without multiple layers of conductive materials on a single conductor, the possibilities of usage available to those skilled in the art are too numerous to mention but are contemplated as a result of the combination of features and advantages of the present invention.

For an appreciation of the scope of the present invention, the claims follow.

What is claimed is:

1. A single biomedical electrode having a first portion and a second portion on the single electrode to provide a differing electrochemical potential, wherein the single electrode has a combination of the first portion and the second portion selected from the group consisting of (a) at least two electrical conductors of differing compositions contacting one field of ionically conductive medium of conductive hydrogel or adhesive, wherein one of the differing compositions is carbon or an inorganic oxide and the other differing composition is a metal and wherein one electrical conductor is on the first portion and wherein one other electrical conductor is on the second portion, (b) at least two fields of ionically conductive media of differing compositions of hydrogel or adhesive wherein one field of ionically conductive medium is on first portion and wherein one other ionically conductive medium is on the second portion, and (c) at least two electrical conductors of differing compositions contacting at least two fields of ionically conductive media of differing compositions of hydrogel or adhesive wherein one electrical conductor is on the first portion and wherein one other electrical conductor is on the second portion; wherein one field of ionically conductive medium is on the first portion and wherein one other ionically conductive medium is on the second portion.

2. The biomedical electrode of claim 1, wherein one conductor on the first portion is more galvanically active than the other electrical conductor or conductors on the second portion.

3. The biomedical electrode of claim 2, wherein one conductor on the first portion is more electron donating than the other electrical conductor or conductors on the second portion.

4. The biomedical electrode of claim 1, wherein one conductor on the first portion contains a galvanically active material and the other electrical conductor or conductors on the second portion contain(s) a galvanically inactive material.

5. The biomedical electrode of claim 1, wherein the electrical conductors on the first portion and the second portion are contiguous and are covered by discontiguous fields of ionically conductive media on the first portion and the second portion.

6. The biomedical electrode of claim 1, wherein the electrical conductors on the first portion and the second portion are discontiguous and are covered by a single field of ionically conductive medium on the first portion and the second portion.

7. The biomedical electrode of claim 1, wherein the electrical conductors on the first portion and the second portion are contiguous and are covered by a single field of ionically conductive medium on the first portion and the second portion.

8. The biomedical electrode of claim 1, wherein one electrical conductor on the first portion has an aperture and is covered by a field of ionically conductive medium and wherein the other conductor on the second portion is a separate biomedical electrode residing in the aperture.

9. The biomedical electrode of claim 1, wherein at least one conductor on the first portion comprises one layer of electrically conductive material and a second layer of electrically conductive material contacting the first layer and contacting a field of ionically conductive medium.

10. The biomedical electrode of claim 1, wherein one field of ionically conductive medium on the first portion comprises an oxidizable species and the other field of ionically conductive medium on the second portion comprises a reducible species.

11. The biomedical electrode of claim 1, wherein one field of ionically conductive medium comprises species for one conductor on the first portion and the other field of ionically conductive medium comprises a species that will form chemical bonds with ions from a second conductor on the second portion.

12. A method of using the biomedical electrode of claim 1, comprising the step of connecting the electrode with a body of a patient, wherein one conductor on the first portion serves to deliver therapy comprising electrical signals to a body of a patient or as a dispersive plate for electrosurgery and wherein one other conductor on the second portion serves to receive bioelectrical signals from the body of the patient.

13. The use of claim 12, wherein each of the conductors on the first portion and the second portion of the electrode provides a different function of the electrode in connection with the body of a patient.

14. The method of claim 12, wherein the delivering therapy is selected from the group consisting of transcutaneous electrical nerve stimulation, iontophoresis, skin conditioning, cardiac pacing, transdermal drug, delivery, transdermal electrical anesthesia, electrophysiological assessment, and combinations thereof.

15. The use of claim 12, wherein the delivering therapy employs the biomedical electrode of claim 2 in a galvanic circuit.

16. The use of claim 12, wherein one conductor on the first portion serves to provide identification or status information to biomedical instrumentation and wherein one other conductor on the second portion serves to receive bioelectrical signals from the body of the patient.

17. The use of claim 12, wherein the conductors on the first portion and on the second portion serve to create a galvanic battery and at least one conductor serves to receive bioelectrical signals from the body of the patient.

18. The use of claim 12, wherein the conductors on the first portion and on the second portion serve to create a galvanic battery and at least one conductor serves to deliver electrical signals to the body of the patient.

19. The use of claim 12, wherein the conductors on the first portion and on the second portion serve to create a galvanic battery and at least one conductor serves to receive bioelectrical signals from the body of the patient and at least one other conductor serves to create or restore a defibrillation recovery surface on the conductor receiving bioelectrical signals.

20. The method of claim 12, wherein the conductors on the first portion and on the second portion are restored to a monitoring function after defibrillation of a heart of a patient by electrical energy delivered from a galvanic circuit formed in the electrode or from biomedical instrumentation.

21. The method of claim 12, wherein the fields of ionically conductive media on the first portion and on the second portion are restored to a monitoring function after defibrillation of a heart of a patient by electrical energy delivered from a galvanic circuit formed in the electrode or from biomedical instnumentation.

22. The method of claim 12, wherein the conductors on the first portion and on the second portion are contiguous, the ionically conductive media are separate fields on the first portion and on the second portion, and a galvanic circuit is created by different compositions of the conductors, the separate fields of ionically conductive media, and the body of the patient.

23. The use of claim 12, wherein the conductors on the first portion and on the second portion are discontiguous and a galvanic circuit is created by different compositions of the conductors, a single field of ionically conductive media, and an electrical connector between the discontiguous conductors.

* * * * *

UNITED STATES PATENT AND TRADEMARK OFFICE
CERTIFICATE OF CORRECTION

PATENT NO.: 6,135,953
DATED: October 24, 2000
INVENTOR(S): Hatim M. Carim

It is certified that error appears in the above-identified patent and that said Letters Patent is hereby corrected as shown below:

Claim 13, Col. 12, Line 9, "method" should read -- use --.

Claim 15, Col. 12, Line 19, "method" should read -- use --.

Claim 16, Col. 12, Line 22, "method" should read -- use --.

Claim 17, Col. 12, Line 27, "method" should read -- use --.

Claim 18, Col. 12, Line 31, "method" should read -- use --.

Claim 19, Col. 12, Line 35, "method" should read -- use --.

Claim 21, Col. 12, Line 52, "instnumentation" should read -- instrumentation --.

Claim 23, Col. 12, Line 60, "method" should read -- use --.

Signed and Sealed this

Twenty-ninth Day of May, 2001

Attest:

NICHOLAS P. GODICI

*Attesting Officer*  *Acting Director of the United States Patent and Trademark Office*